United States Patent [19]
McKenna et al.

[11] Patent Number: 5,800,341
[45] Date of Patent: Sep. 1, 1998

[54] ELECTRONICALLY STEERABLE ENDOSCOPE

[75] Inventors: Michael A. McKenna, Cambridge, Mass.; Joseph M. Rosen, Hanover, N.H.; David T. Chen, Somerville, Mass.; Steven D. Pieper, Thetford Center; Peter J. Robbie, Norwich, both of Vt.

[73] Assignee: Medical Media Systems, West Lebanon, N.H.

[21] Appl. No.: 464,380

[22] Filed: Jun. 5, 1995

Related U.S. Application Data

[62] Division of Ser. No. 220,367, Mar. 30, 1994, Pat. No. 5,547,455.

[51] Int. Cl.⁶ .................................................. A61B 1/05
[52] U.S. Cl. .......................... 600/109; 600/129; 600/173; 348/65
[58] Field of Search .................. 600/103, 109, 600/173, 129; 348/36, 39, 65, 143, 207, 240

[56] References Cited

U.S. PATENT DOCUMENTS

| | | |
|---|---|---|
| 3,889,662 | 6/1975 | Mitsui . |
| 4,699,463 | 10/1987 | D'Amelio et al. . |
| 4,816,909 | 3/1989 | Kimura et al. ................ 600/109 |
| 4,846,154 | 7/1989 | MacAnally et al. . |
| 4,873,572 | 10/1989 | Miyazaki et al. . |
| 4,991,020 | 2/1991 | Zwirn ........................ 348/207 |
| 5,025,778 | 6/1991 | Silverstein et al. . |
| 5,166,787 | 11/1992 | Irion . |
| 5,301,061 | 4/1994 | Nakada et al. . |
| 5,313,306 | 5/1994 | Kuban et al. . |
| 5,335,662 | 8/1994 | Kimura et al. . |
| 5,398,685 | 3/1995 | Wilk et al. . |
| 5,430,475 | 7/1995 | Goto et al. ..................... 348/65 |

FOREIGN PATENT DOCUMENTS 305170  8/1988  European Pat. Off. .

*Primary Examiner*—John P. Leubecker
*Attorney, Agent, or Firm*—Pandiscio & Pandiscio

[57] ABSTRACT

A multiple view endoscope provides "on command" images of a plurality of different fields of view surrounding the distal end of the endoscope without having to move the endoscope from an initially established position in order to access the different fields of view. In one embodiment, a CCD element comprising a plurality of CCD cells forms a circumferential band about the distal portion of the endoscope. In another embodiment, the plurality of CCD cells covers substantially all of the outer side wall of the shaft adjacent to the distal end. In both embodiments, a processing device functions to either use the outputs from all the CCD cells to generate a display image or use the outputs from only selected ones of the CCD cells to generate a display image of a selected portion of the entire image captured by the CCD element.

5 Claims, 12 Drawing Sheets

| IMAGE FROM IMAGE CAPTURING MEANS 55A | IMAGE FROM IMAGE CAPTURING MEANS 55B | IMAGE FROM IMAGE CAPTURING MEANS 55B | IMAGE FROM IMAGE CAPTURING MEANS 55A |
|---|---|---|---|
| | | IMAGE FROM IMAGE CAPTURING MEANS 55F | IMAGE FROM IMAGE CAPTURING MEANS 55E |

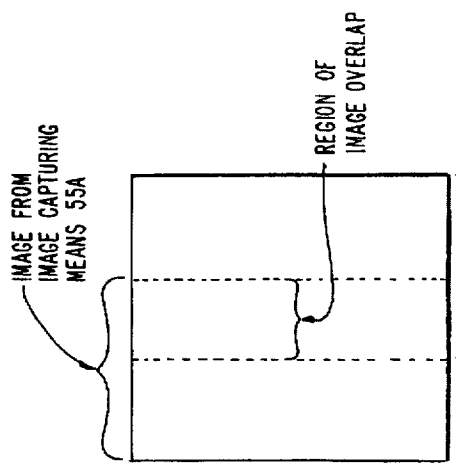
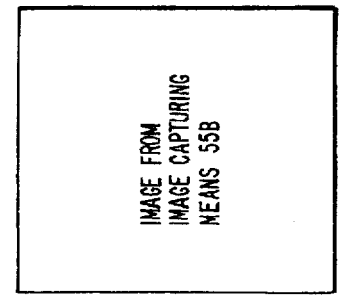
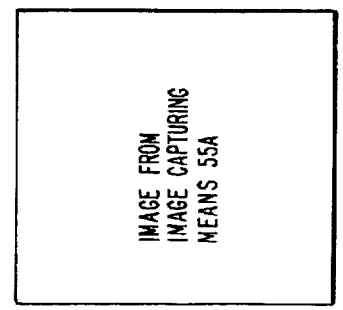
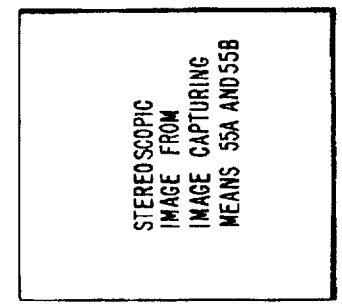
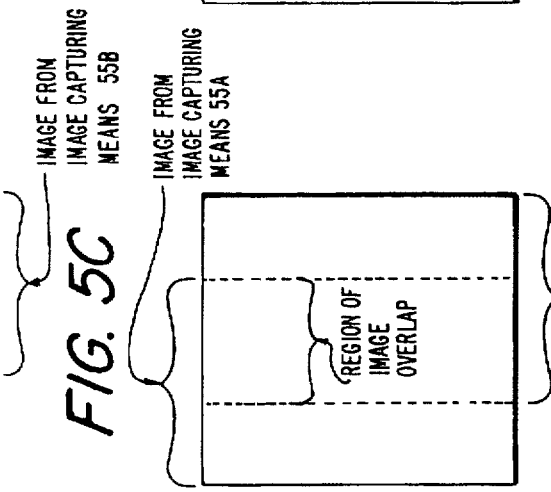
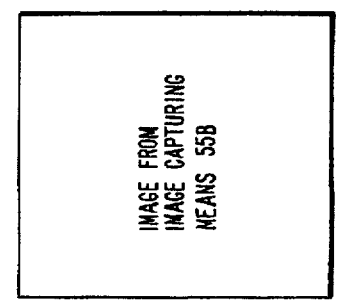
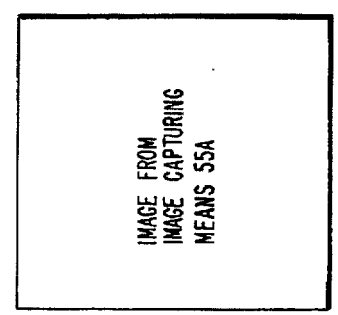

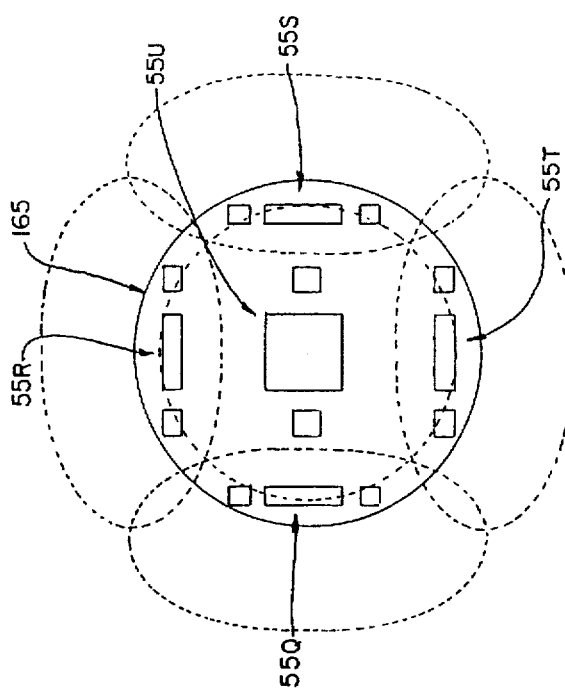
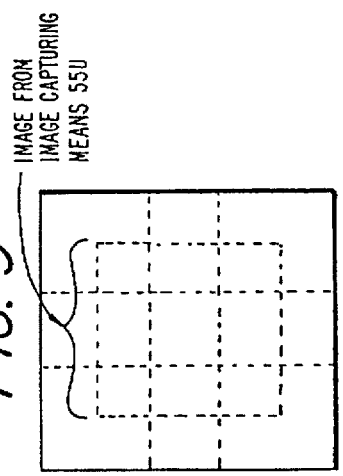
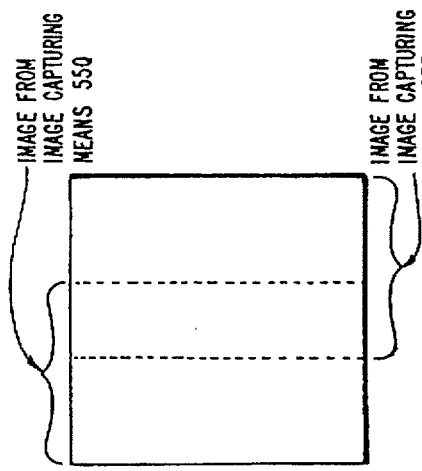
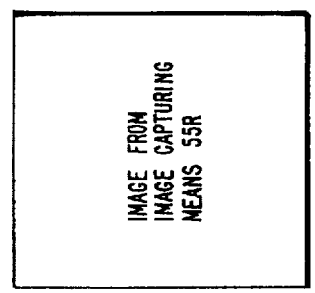
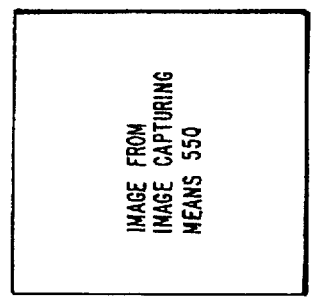

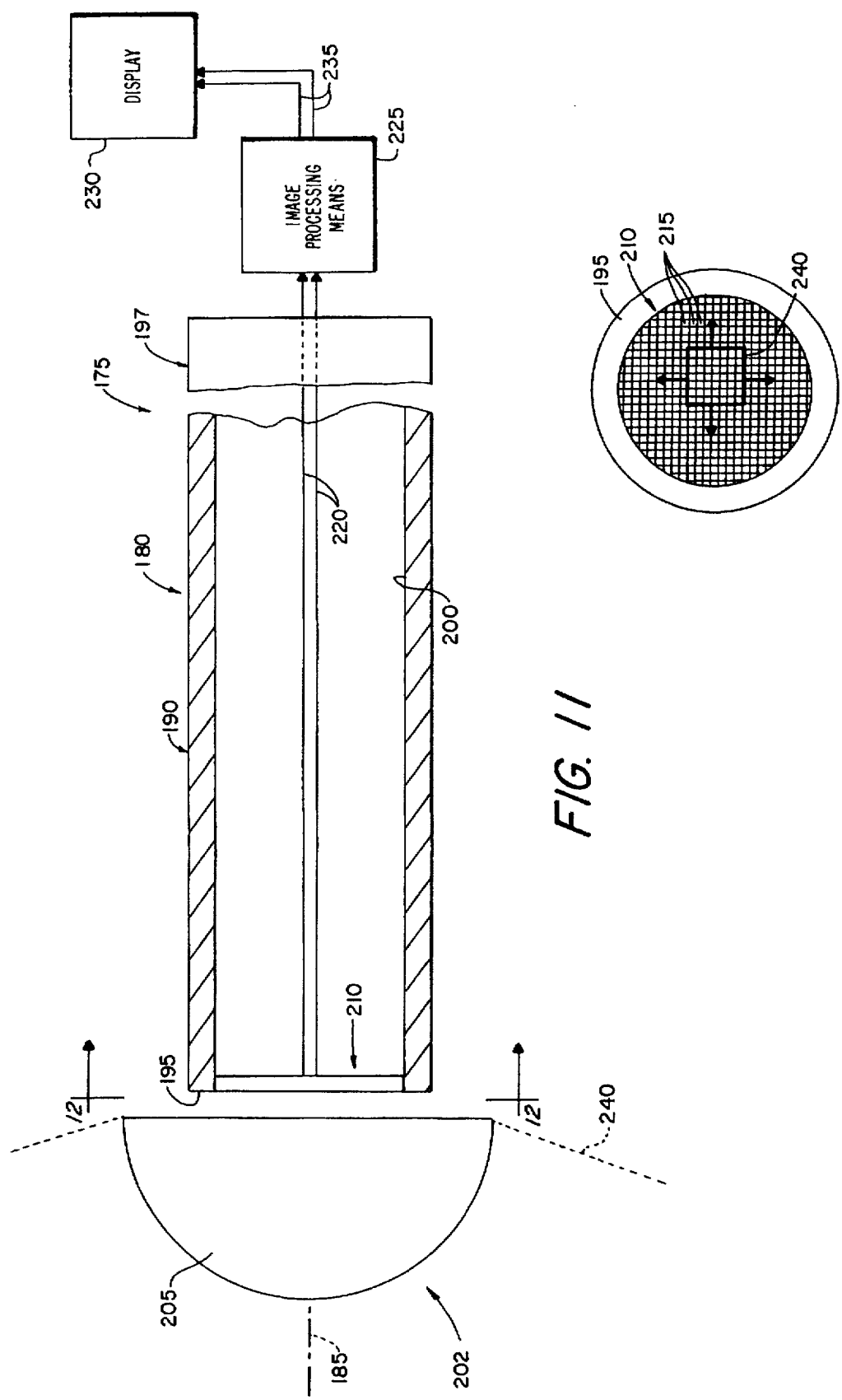

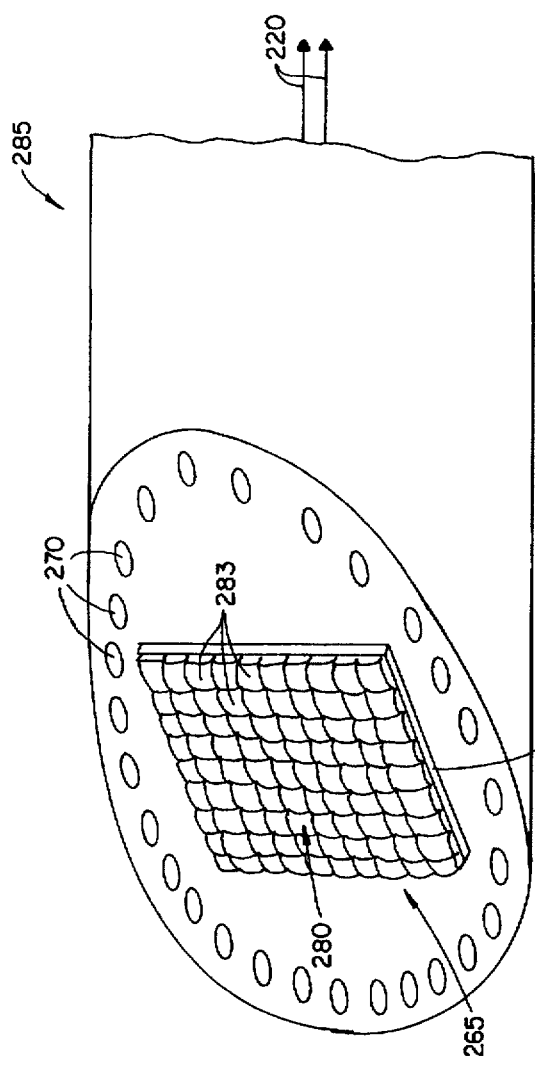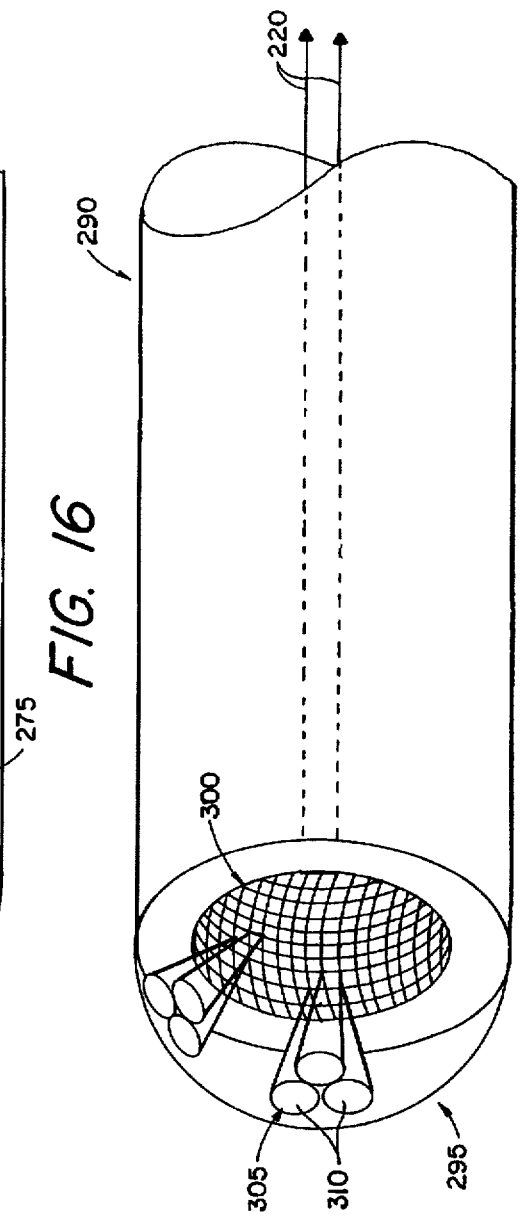
FIG. 16
FIG. 17

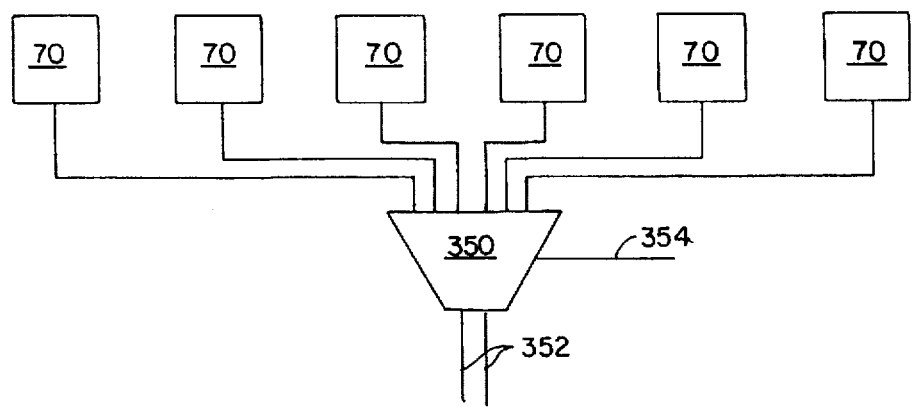
FIG. 21
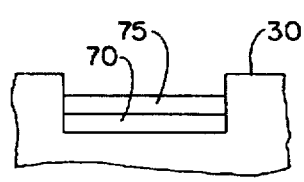 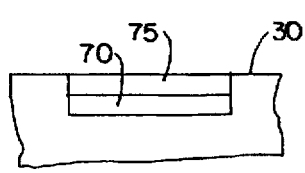 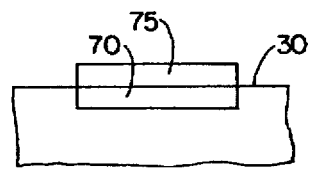
FIG. 22   FIG. 23   FIG. 24

ELECTRONICALLY STEERABLE ENDOSCOPE

This is a division of U.S. application Ser. No. 08/220,367, filed Mar. 30, 1994 for "Electronically Steerable Endoscope" now U.S. Pat. No. 5,547,455.

FIELD OF THE INVENTION

This invention relates to viewing devices in general, and more particularly to endoscopes and the like.

BACKGROUND OF THE INVENTION

Endoscopic viewing devices are well known in the art. In general, such devices are used to view the interior of limited access spaces such as body cavities, the interiors of complex machinery, etc. Endoscopic viewing devices generally comprise an elongated shaft having a distal end and a proximal end, and at least one internal passageway extending between the distal end and the proximal end. The shaft may be rigid or flexible, depending on the particular application involved. Image capturing means extend through the shaft's at least one internal passageway and are adapted to capture an image of a selected region located substantially adjacent to the distal end of the shaft, and to convey that image to a viewing device disposed at the proximal end of the shaft. In order to assist viewing, illumination means are also typically provided on the endoscope. The illumination means also extend through the shaft's at least one internal passageway and are adapted to project light onto the region to be viewed by the image capturing means.

The image capturing means commonly utilize one of several different arrangements to capture an image at the distal end of the shaft and to convey it to a viewing device located at the proximal end of the shaft.

In one arrangement, the image capturing means comprise a bundle of fiber optic filaments extending through the shaft's at least one internal passageway. An appropriate lens is positioned at the distal end of the shaft to focus the desired image onto the distal end of the fiber optic bundle. A conventional optical viewer or eyepiece is positioned at the proximal end of the shaft to receive the image conveyed to the proximal end of the fiber optic bundle. Alternatively, an appropriate image sensor, such as a charge coupled device ("CCD") element or video tube, may be positioned at the proximal end of the shaft to receive the image conveyed to the proximal end of the fiber optic bundle. Wires then connect the image sensor to an adjacent viewing device.

In a second arrangement, the image capturing means comprise a CCD element disposed at the distal end of the shaft. An appropriate lens focuses the desired image onto the CCD element's light-receiving surface, and wires extend through the shaft's at least one internal passageway to connect the endoscope's CCD element to a viewing device located adjacent to the proximal end of the shaft.

In a third arrangement, the image capturing means comprise a so-called rod-lens system. In this embodiment, a series of rod lens elements are arranged within the shaft's at least one internal passageway so as to capture the desired image at the distal end of the shaft and convey it to the proximal end of the shaft. A conventional optical viewer or eyepiece is positioned at the proximal end of the shaft to receive the image which is conveyed to the proximal end of the rod-lens system. Alternatively, an appropriate image sensor, such as a charge coupled device ("CCD") element or video tube, may be positioned at the proximal end of the shaft to receive the image conveyed to the proximal end of the rod-lens system. Wires then connect the image sensor to an adjacent viewing device.

The illumination means commonly comprise apparatus for conveying light from a light source disposed at the proximal end of the shaft to an exit point located at the distal end of the shaft. For example, the illumination means frequently comprise a bundle of fiber optic filaments extending through the shaft's at least one internal passageway.

In practice, endoscopic viewing devices have taken on several common forms. More specifically, endoscopic viewing devices have been designed such that either (i) the image capturing means open onto the distal end of the shaft so as to face distally therefrom; (ii) the image capturing means open onto the distal end of the shaft so as to face outwardly therefrom at fixed or movable oblique angles; (iii) the image capturing means are disposed relative to the distal end of the shaft as set forth in categories (i) or (ii) above and the distal end of the shaft is itself deflectable relative to its longitudinal axis (i.e., the shaft is "steerable"); (iv) the image capturing means open onto the side wall of the shaft substantially adjacent to its distal end surface; or (v) the distal end of the shaft is affixed to a surgical instrument substantially adjacent to the working end of the surgical instrument.

Examples of endoscopes exhibiting the characteristics of the aforementioned category (i) are shown in the following U.S. patents:

| U.S. Pat. No. | Issued | To |
| --- | --- | --- |
| 1,345,406 | 7/6/20 | Rimmer |
| 3,581,738 | 6/1/71 | Moore |
| 4,245,624 | 1/20/81 | Komiya |
| 4,419,987 | 12/13/83 | Ogiu |
| 4,445,892 | 5/1/84 | Hussein et al. |
| 4,461,283 | 7/24/84 | Doi |
| 4,606,330 | 8/19/86 | Bonnet |
| 4,617,915 | 10/21/86 | Arakawa |
| 4,641,912 | 2/10/87 | Goldenberg |
| 4,662,368 | 5/5/87 | Hussein et al. |
| 4,672,963 | 6/16/87 | Barken |
| 4,718,406 | 1/12/88 | Bregman et al. |
| 4,740,047 | 4/26/88 | Abe et al. |
| 4,770,653 | 9/13/88 | Shturman |
| 4,788,975 | 12/6/88 | Shturman et al. |
| 4,798,193 | 1/17/89 | Giesy et al. |
| 4,874,371 | 10/17/89 | Comben et al. |
| 4,887,600 | 12/19/89 | Watson et al. |
| 4,899,733 | 2/13/90 | DeCastro et al. |

Still another example of an endoscope exhibiting the characteristics of the aforementioned category (i) is shown in Soviet Union Patent Document No. SU 1020-124-A dated Mar. 27, 1981.

All of the foregoing patents are incorporated herein by reference.

Examples of endoscopes exhibiting the characteristics of the aforementioned category (ii) are shown in the following U.S. patents:

| U.S. Pat. No. | Issued | To |
| --- | --- | --- |
| 4,175,545 | 11/27/79 | Termanini |
| 4,418,688 | 12/6/83 | Loeb |
| 4,784,132 | 11/15/88 | Fox et al. |
| 4,800,876 | 1/31/89 | Fox et al. |
| 5,127,393 | 7/7/92 | McFarlin et al. |

All of the foregoing patents are also incorporated herein by reference.

Examples of endoscopes exhibiting the characteristics of the aforementioned category (iii) are shown in the following U.S. patents:

| U.S. Pat. No. | Issued | To |
| --- | --- | --- |
| 3,886,933 | 6/3/75 | Mori et al. |
| 4,648,892 | 3/10/87 | Kittrell et al. |
| 4,669,467 | 6/2/87 | Willett et al. |
| 4,911,148 | 3/27/90 | Sosnowski et al. |
| 4,996,974 | 3/5/91 | Clariei |
| 5,083,549 | 1/28/92 | Cho et al. |

All of the foregoing patents are also incorporated herein by reference.

Examples of endoscopes exhibiting the characteristics of the aforementioned category (iv) are shown in the following U.S. patents:

| U.S. Pat. No. | Issued | To |
| --- | --- | --- |
| 4,277,168 | 7/7/81 | Oku |
| 4,375,818 | 3/8/83 | Suwaki et al. |
| 4,699,463 | 10/13/87 | D'Amelio et al. |
| 4,905,667 | 3/6/90 | Foerster et al. |

More particularly, the Oku patent shows a side view endoscope which is designed to be rotated about its longitudinal axis by a pair of parallel, rigid wires which extend through the endoscope's shaft and are affixed to the distal end of the shaft. A first bundle of fiber optic filaments (i.e., the illumination means) conveys light from a light source located adjacent to the proximal end of the shaft to a first opening formed in the side wall of the shaft adjacent to its distal end surface. A second bundle of fiber optic filaments (i.e., the image capturing means) gathers an image from a mirror and lens arrangement disposed at a second opening located in the side wall of the shaft adjacent to the first opening, and conveys the same to a viewing device located at the proximal end of the shaft. The rotational position of the shaft is tracked relative to an outer sheath by third and fourth bundles of fiber optic filaments, which extend from the proximal end of the shaft to a third opening formed in the side wall of the shaft. The third opening is spaced proximally from the first and second openings and faces the interior of the outer sheath. The third bundle of fiber optic filaments is used to illuminate the portion of the outer sheath located adjacent to the shaft's third opening, and the fourth bundle of fiber optic filaments is used to view the portion of the outer sheath located adjacent to the shaft's third opening. Using the third and fourth bundles of fiber optic filaments, the operator can monitor rotation of the shaft's third opening past graduated markings on the inner surface of the outer sheath, etc. so as to determine the rotational position of the shaft relative to the outer sheath.

The Suwaki et al. patent shows a side view endoscope including an ultrasonic diagnosis system. With this endoscope, side viewing is provided by means similar to those provided by the Oku patent, i.e., a first bundle of fiber optic filaments (i.e., the illumination means) projects light out of a first opening in the shaft, and a second bundle of fiber optic filaments (i.e., the image capturing means) gathers an image from a mirror and lens arrangement disposed at a second opening in the shaft and conveys the same to the proximal end of the shaft. In addition, a third opening is provided in the side wall of the endoscope in adjacent, axially-spaced relation to the first and second openings. An ultrasonic wave generator is adapted to emit ultrasonic waves out of the shaft's third opening and against adjacent tissue as that tissue is illuminated and viewed by the first and second bundles of fiber optic filaments, respectively.

The D'Amelio patent shows an endoscope of the type exhibiting the characteristics of the aforementioned category (i), i.e., an endoscope adapted for distally directed viewing. In addition, however, a cap member is also provided at the distal end of the shaft. This cap member is rotatable relative to the shaft and contains both an axially directed passageway and a generally L-shaped passageway having a mirror disposed at the inside corner of the "L". As a result of this construction, when the cap is turned so that its axial passageway is aligned with the endoscope's viewing system, the device allows an axially positioned field to be viewed. At the same time, when the cap is turned so that its L-shaped passageway is aligned with the endoscope's viewing system, the device allows a radially positioned field to be viewed.

The Foerster et al. patent discloses a side view duodenoscope, but does not specifically disclose the means by which the side viewing capability of the scope is provided.

All of the foregoing patents are also incorporated herein by reference.

Finally, an example of an endoscope exhibiting the characteristics of the aforementioned category (v) is shown in U.S. Pat. No. 4,759,348 issued Jul. 26, 1988 to Cawood.

This patent is also incorporated herein by reference.

In view of the foregoing, it will be appreciated that some endoscopic viewing systems currently exist which permit the operator to view fields located in axial alignment with the distal end of the shaft, while other endoscopic viewing systems currently exist which permit the operator to view fields located at various angles to the longitudinal axis of the endoscope.

In addition to the foregoing, endoscopic viewing devices have also been developed for stereoscopically viewing objects located in axial alignment with the distal end of the endoscope. These devices generally utilize a pair of viewing systems like those discussed above with respect to the aforementioned category (i) devices, but with the two viewing systems arranged so as to have the same or largely overlapping fields of view. The images from each of the two viewing systems are combined in the endoscope's display so as to provide the operator with a stereoscopic view of any objects and/or structures located within the common viewing field.

Unfortunately, none of the foregoing endoscopic viewing systems is entirely satisfactory.

More particularly, it should be appreciated that the field of view for all of the foregoing endoscopic viewing devices is generally quite limited in scope, relative to the size of the anatomy or region which is typically under examination. Fortunately, in many situations the operator can compensate for this simply by moving the endoscope about the surgical site or other volume of interest. For example, the operator may move the entire endoscope proximally or distally, or the operator may rotate the scope about its longitudinal axis, or the operator may combine these two actions. It has been found in many applications that by moving the endoscope about in this way, substantially the entire surgical site can be viewed through the endoscope.

In some situations such as those where the primary goal of a procedure is visual examination, the foregoing capabilities may be adequate. In other situations such as laparoscopic surgical procedures, however, it is generally difficult for the surgeon to simultaneously manipulate both the surgical instruments needed to perform the surgical procedure and the endoscope needed to view the procedure. As a result, another person must generally assist the surgeon by manipulating either one or more of the surgical instruments and/or the endoscope in coordination with the surgeon.

The device discussed above with respect to the aforementioned category (v) attempts to alleviate this problem by attaching the viewing head of the endoscope directly onto the working end of the surgical instrument. Unfortunately, however, this arrangement is not totally satisfactory. For one thing, it does not provide the surgeon with a view of any objects and/or structures which may be somewhat removed from the working end of the surgical instrument, nor does it permit the surgeon to have a "bird's eye" (or "third person") view of the surgical instrument while that instrument is being used in surgery.

Furthermore, in many applications it may be difficult or even impossible to move the endoscope about the surgical site so as to compensate for the endoscope's limited field of view. For example, the surgical site might be a highly confined region or include hard to reach locations. Also, the surgical site might be surrounded by delicate tissue such that endoscope movement should be minimized.

Accordingly, an improved endoscopic viewing system is needed which can provide "on command" images of one or more fields of view surrounding the distal end of the endoscope, without the need for any physical manipulation of the endoscope whatsoever from an initially established position. The provision of such a device would minimize or eliminate the need to move the endoscope about the surgical site during a procedure, while still providing the surgeon with an excellent view of the entire surgical site and any objects and/or structures located in the vicinity of the surgical site.

OBJECTS OF THE INVENTION

Accordingly, one object of the present invention is to provide an improved endoscope which includes image capturing means for providing "on command" images of a plurality of different fields of view surrounding the distal end of the endoscope, without having to move the endoscope from an initially established position in order to access the different fields of view.

Another object of the present invention is to provide a "multiple view" endoscope which comprises viewing means adapted to allow an operator to select and view either any one of, or any combination of, the multiple views provided by the endoscope.

Still another object of the present invention is to provide a "multiple view" endoscope which comprises a plurality of image capturing means associated with the distal end of the endoscope, wherein each of the image capturing means is connected to viewing means located adjacent to the proximal end of the endoscope by connecting means extending through the shaft of the endoscope.

Yet another object of the present invention is to provide a "multiple view" endoscope which comprises a plurality of image capturing means associated with the distal end of the endoscope, and a plurality of illumination means also associated with the distal end of the endoscope, wherein each of the image capturing means is adapted to capture an image of any objects and/or structures located within a predetermined field of view relative to the distal end of the endoscope and to transmit that image to the proximal end of the endoscope, and wherein the plurality of illumination means are adapted to project light onto the various fields of view of the image capturing means.

Still another object of the present invention is to provide a "multiple view" endoscope which comprises a plurality of image capturing means associated with the distal end of the endoscope, and a plurality of illumination means associated with the distal end of the endoscope, wherein one of the illumination means is paired with each one of the image capturing means so as to properly illuminate the field of view for that image capturing means.

Another object of the present invention is to provide a "multiple view" endoscope which comprises a plurality of non-visual sensor means associated with the distal end of the endoscope, wherein each non-visual sensor means comprises ultrasound sensors for providing additional non-visual information regarding any objects and/or structures able to be viewed by the endoscope.

And another object of the present invention is to provide a "multiple view" endoscope which comprises a plurality of non-visual sensor means associated with the distal end of the endoscope, wherein each non-visual sensor means comprises electromagnetic transceivers, temperature sensors, chemical sensors, etc. for providing additional non-visual information regarding any objects and/or structures within the same general region as the distal end of the endoscope.

Still another object of the present invention is to provide a "multiple view" endoscope which comprises a plurality of image capturing means associated with the distal end of the endoscope, wherein each of the image capturing means comprises at least one CCD element, the at least one CCD element being adapted to capture an image of any objects and/or structures located within the predetermined field of view for that particular image capturing means and to convert that image into corresponding electrical signals, and further wherein the endoscope comprises connecting means for conveying those corresponding electrical signals through the shaft of the endoscope to image processing means disposed adjacent to the proximal end of the endoscope.

Yet another object of the present invention is to provide a "multiple view" endoscope which comprises a plurality of image capturing means associated with the distal end of the endoscope, and a plurality of illumination means associated with the distal end of the endoscope, wherein each of the image capturing means and each of the illumination means is connected to the proximal end of the endoscope by separate connecting means extending through the endoscope's shaft.

Another object of the present invention is to provide a "multiple view" endoscope which comprises a plurality of image capturing means associated with the distal end of the endoscope, and a plurality of illumination means associated with the distal end of the endoscope, wherein each of the image capturing means and each of the illumination means is connected to the proximal end of the endoscope by separate connecting means extending through the endoscope's shaft, and further wherein the endoscope's shaft comprises a plurality of longitudinally-extending internal passageways, and each of the connecting means extends from its associated image capturing means or its associated illumination means to the proximal end of the endoscope through a preselected one of said interior passageways.

Still another object of the present invention is to provide a "multiple view" endoscope comprising a plurality of image capturing means associated with the distal end of the endoscope, a plurality of illumination means associated with the distal end of the endoscope, and a plurality of non-visual sensor means associated with the distal end of the endoscope, wherein one of the image capturing means is grouped with one of the illumination means and one of the non-visual sensor means so as to form a distinct group directed approximately in the same direction relative to the distal end of the endoscope, and further wherein the endoscope comprises viewing means associated with the proximal end of the endoscope for receiving and displaying image information received from one or more of the endoscope's image capturing means, along with non-visual information received from one or more of the endoscope's non-visual sensor means.

Still another object of the present invention is to provide an improved endoscope which can be used in both medical and industrial applications.

And another object of the present invention is to provide an endoscope which comprises a plurality of image capturing means associated with the distal end of the endoscope, wherein the plurality of image capturing means may or may not all be of the same type as one another.

Yet another object of the present invention is to provide an improved endoscope wherein the endoscope's field of view can be altered without physically moving the endoscope from an established position.

SUMMARY OF THE INVENTION

These and other objects are addressed by the present invention, which comprises a novel "multiple-view" endoscope and the use of the same. The "multiple-view" endoscope comprises an elongated shaft having a distal end terminating in a distal end surface, a proximal end, and an outer side wall extending between the distal end and the proximal end. The shaft may or may not be flexible, depending on the particular application involved. One or more internal passageways extend from the distal end of the shaft to the proximal end of the shaft.

A plurality of image capturing means are associated with the distal end of the shaft, i.e., they are either disposed on the distal end surface of the shaft so as to face outboard therefrom, and/or they are disposed on the outer side wall of the shaft so as to face outboard therefrom. Preferably at least some of the image capturing means are disposed on the outer side wall of the shaft.

Each of the image capturing means comprises means for capturing an image of any objects and/or structures located within a predetermined field of view relative to the distal end of the shaft. Preferably a sufficient number of image capturing means are provided so that their individual fields of view will collectively provide complete coverage of the region surrounding the distal end of the endoscope.

Each of the image capturing means may comprise a charge coupled device ("CCD") element and an associated lens means where the CCD element is adapted to capture an image of any objects and/or structures located within the field of view established by its associated lens means and to convert the same into corresponding electrical signals. Connecting means extend through the shaft of the endoscope to convey these corresponding electrical signals to image processing means disposed adjacent to the proximal end of the endoscope, for display to the operator of the system.

Alternatively, each of the image capturing means may comprise a bundle of elongated fiber optic filaments extending between an appropriate lens means disposed at the distal end of the endoscope and the proximal end of the endoscope. These fiber optic filaments are adapted to capture an image of any objects and/or structures located within the field of view established by the lens means and to deliver the same to the proximal end of the endoscope. At the proximal end of the endoscope, the image conveyed by the fiber optic filaments is received by a CCD element which is adapted to convert that image into corresponding electrical signals. These corresponding electrical signals are then transmitted to appropriate image processing means also located at the proximal end of the endoscope, for display to the operator of the system.

Or each of the image capturing means may comprise a so-called rod-lens system in which a series of rod-lens elements are arranged within the shaft's at least one internal passageway so as to capture the desired image at the distal end of the shaft and convey it to the proximal end of the shaft. At the proximal end of the shaft, the image conveyed by the rod-lens system is received by a CCD element which is adapted to convert that image into corresponding electrical signals. These corresponding electrical signals are then transmitted to appropriate image processing means also located at the proximal end of the endoscope, for display to the operator of the system.

If desired, the endoscope's image capturing means may all be of the same type. Alternatively, the endoscope's image capturing means may comprise two or more different types of devices.

The image processing means generally comprise a preprogrammed digital computer. The image processing means are adapted to receive the image information conveyed by the plurality of image capturing means and to convey the same to a display screen and/or other visual output means for display to the operator of the system and/or to a recording device such as a VCR for subsequent viewing, or to computer memory for subsequent processing and/or analysis. The display may be of a single image associated with a selected one of the image capturing means, or it may be of a tiled plurality of such images associated with two or more different image capturing means, or it may be of an overlapping combination of such images associated with two or more different image capturing means. The latter alternative is particularly useful in those situations where the viewing field for a selected one of the image capturing means significantly overlaps the viewing field of at least one adjacent image capturing means. In such a case, the overlapping images can be appropriately formatted and displayed so as to provide a stereoscopic image of any objects and/or structures located in the overlapping fields of view.

Illumination for the viewing fields of the endoscope's various image capturing means may be provided by a separate and distinct lighting instrument if desired. More preferably, however, the endoscope of the present invention also comprises illumination means for projecting light onto any objects and/or structures located in its various viewing fields. The illumination means generally comprise at least one source of light adapted to shine outwardly from the distal end of the endoscope so as to illuminate the regions covered by the endoscope's image capturing means. The illumination means may comprise a light mounted within the distal end of the endoscope adjacent to at least one opening formed therein, with the light being electrically connected to a power source at the proximal end of the endoscope by wires extending through the shaft. More preferably, however, the illumination means comprise a light source located at the proximal end of the endoscope, and a plurality of elongated fiber optic filaments extending through the shaft from the light source to at least one opening formed in the distal end of the endoscope. In this way light from the light source will enter the proximal end of the fiber optic filaments and be transmitted along the filaments so as to exit the endoscope through the at least one opening formed in the distal end of the shaft. Preferably, each of the at least one openings also includes a light diffusing lens associated therewith, so that light exiting from the distal ends of the fiber optic filaments will properly illuminate a predetermined volume extending outwardly from each of the at least one opening formed in the distal end of the endoscope.

In one preferred embodiment of the invention, the illumination means are arranged so that one light projecting opening is associated with each image capturing means, such that the field of view for each image capturing means is properly illuminated. The system may also include a method for selectively activating only those light sources illuminating those fields of view currently being monitored.

In addition to the foregoing, one or more non-visual sensor means may also be provided on the distal end of the endoscope. For example, in some cases it may be advantageous to project ultrasound signals into the regions monitored by the image capturing means, and to read the reflected signals so as to obtain non-visual information regarding any objects and/or structures located within the viewing fields of the image capturing means. In this respect it is to be appreciated that such non-visual sensor means might include ultrasound sensors, temperature sensors, pressure sensors, chemical sensors, radiation sensors or any other type of non-visual sensor desired for a particular application. Where a plurality of non-visual sensor means are provided on the endoscope, the various non-visual sensor means may all be of the same type, or they may include a variety of different types. In one preferred embodiment, the endoscope comprises a plurality of non-visual sensor means, with one of the non-visual sensor means being grouped with each one of the image capturing means so as to cover a common region about the distal end of the endoscope.

The endoscope's image capturing means and, to the extent that they are provided, its illumination means and its non-visual sensor means, may be disposed about the distal end of the endoscope in a variety of different configurations.

Thus, in one embodiment of the invention, the endoscope comprises a plurality of image capturing means, a plurality of illumination means, and a plurality of non-visual sensor means, wherein each of the image capturing means has an illumination means and a non-visual sensor means grouped therewith. Each of these groupings of one image capturing means, one illumination means and one non-visual sensor means is spaced axially and circumferentially from every other grouping, and the respective groupings are sufficient in number, so as to provide substantially complete coverage of the region surrounding the distal end of the endoscope. The respective fields of view for these groupings may or may not overlap, as desired.

In another embodiment of the invention, the endoscope comprises a plurality of image capturing means arranged in a semispherical configuration at the distal end of the shaft.

An embodiment is also disclosed wherein the image capturing means comprise a so-called "fisheye" lens (i.e., a lens having an extremely wide field of view, of up to 180 degrees) disposed at the distal end of the endoscope, and a CCD element comprising an extensive array of CCD cells, with the CCD element being disposed adjacent to the fisheye lens so as to capture the image collected by the fisheye lens. With this arrangement, the fisheye lens can be disposed on the distal end of the endoscope so that it is aligned with the shaft's longitudinal axis, or it can be disposed on the distal end of the endoscope so that it is slanted at an oblique angle relative to the longitudinal axis of the endoscope shaft. Alternatively, the CCD element could be disposed at the proximal end of the endoscope, and light from the fisheye lens could be conveyed to the CCD element via fiber optic filaments or a rod-lens system, in ways well known in the art. If desired, the image processing means can be adapted to correct for any image distortion induced by the very wide angle nature of the fisheye lens, by using appropriate image processing algorithms.

In another embodiment of the invention, each of the image capturing means comprise a so-called "fly's eye" lens array having a plurality of separate focusing elements, and a CCD element comprising an extensive array of CCD cells, with the CCD element being disposed adjacent to the fly's eye lens so as to capture the image collected by the fly's eye lens, with one or more CCD cells being associated with each lens focusing element. The separate focusing elements may have narrow or wide fields of view, such that the fields of view between adjacent focusing elements would be essentially non-overlapping (so that each focusing element covers a unique region with greater clarity and sharpness) or significantly overlapping (so that stereoscopic information is obtained, for example). With this arrangement, a plurality of these image capturing means can be disposed about the distal end of the endoscope, or a single image capturing means can be disposed at an oblique angle relative to the longitudinal axis of the endoscope shaft, or a single image capturing means can be disposed semispherically about the distal end of the endoscope.

And in another embodiment of the invention, the image capturing means comprises a CCD element comprising a continuous array of CCD cells circumferentially surrounding the distal end of the endoscope shaft. In this alternative, circumferentially spaced illumination means, and circumferentially spaced non-visual sensor means, preferably flank the array of CCD cells, with the various elements being disposed in a variety of different configurations.

In each of these embodiments, a large number of different images will be simultaneously generated by the endoscope's numerous image capturing means. The system's image processing means allow the operator to select which one or ones of these images will be displayed at any given time. Therefore, in the case of a laparoscopic surgical procedure, for example, the endoscope of the present invention may be placed into, or adjacent to, the surgical site and then left in place without substantial further movement throughout the procedure. All of the different views that may thereafter be required by the surgeon may then be electronically generated by the system, without substantial further movement of the endoscope about the surgical site.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 5A, 5B and 5C are illustrative views showing various images which may be generated by the endoscope of FIG. 4;

FIGS. 7A, 7B, 7C and 7D are illustrative views showing various images which may be generated by the endoscope of FIG. 6;

FIG. 8 is an illustrative partial side view of the distal end of an endoscope formed in accordance with the present invention, wherein the endoscope has a semispherical distal end surface and a plurality of image capturing means located in spaced relationship to one another about that semispherical distal end surface;

FIG. 9 is an illustrative end view of the distal end of the endoscope shown in FIG. 8;

FIGS. 10A, 10B, 10C and 10D are illustrative views showing various images which may be generated by the endoscope of FIGS. 8 and 9;

FIG. 11 is an illustrative side view showing the distal end of still another endoscope formed in accordance with the present invention, wherein a fisheye lens is disposed at the distal end of the endoscope and a substantially planar CCD element is disposed adjacent to the fisheye lens so as to capture the image collected by the fisheye lens;

FIG. 12 is an illustrative cross-sectional view taken along line 12—12 of FIG. 11;

FIG. 16 is an illustrative side view showing the distal end of yet another endoscope formed in accordance with the present invention, wherein the endoscope comprises a single image capturing means including a fly's eye lens, with the image capturing means being slanted at an oblique angle relative to the longitudinal axis of the endoscope;

FIG. 17 is a view similar to that of FIG. 11, except that the fisheye lens has been replaced by a fly's eye lens, and the substantially planar CCD element has been replaced by a curved CCD element;

FIG. 21 is an illustrative block diagram showing how signals from various CCD elements may be multiplexed so as to facilitate their transmission from image capturing means located at the distal end of the endoscope to the image processing means located at the proximal end of the endoscope;

FIG. 22 is an illustrative side view showing one possible disposition of an image capturing means relative to the side wall of the endoscope;

FIG. 23 is an illustrative side view showing another possible disposition of an image capturing means relative to the side wall of the endoscope; and FIG. 24 is an illustrative side view showing still another possible disposition of an image capturing means relative to the side wall of the endoscope.

DETAILED OF THE PREFERRED EMBODIMENTS

Figure 1:
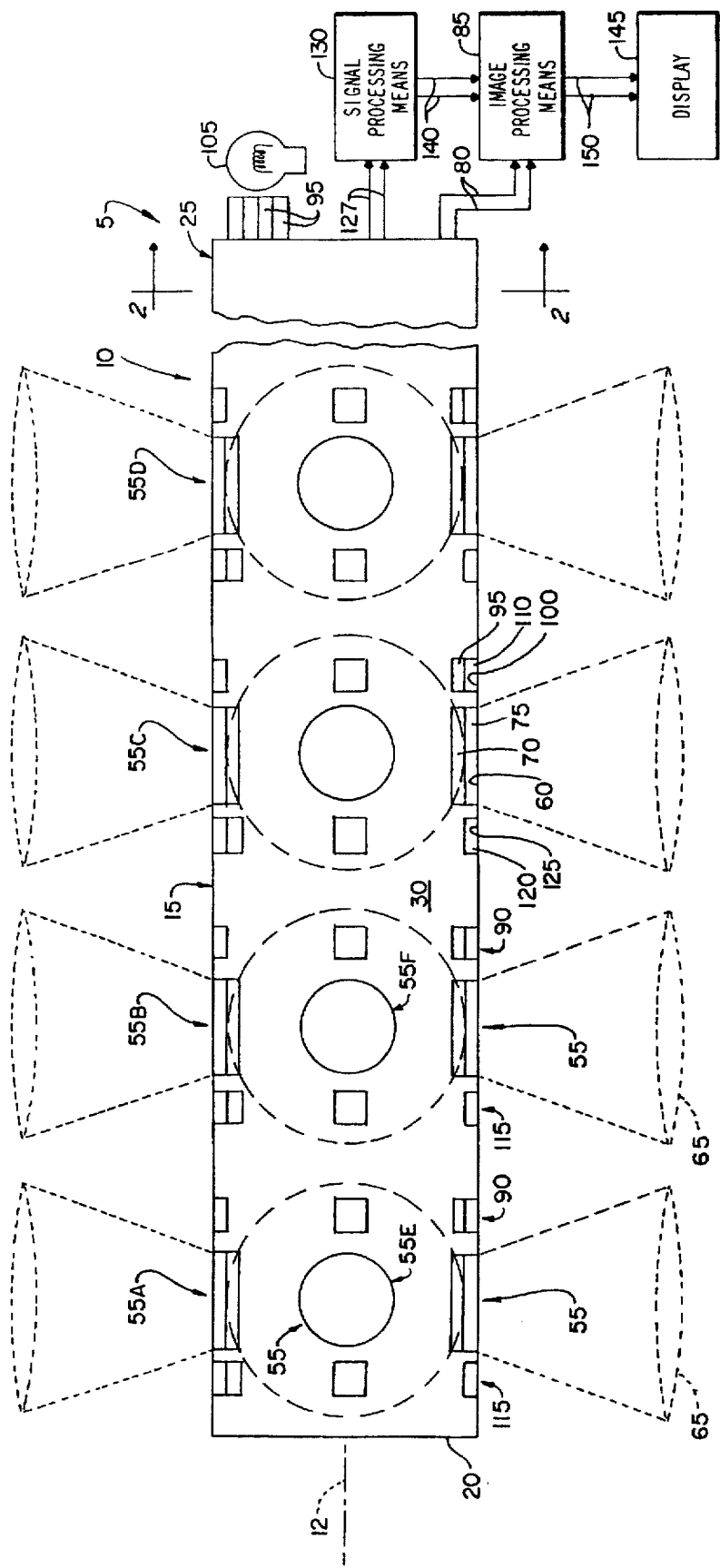
FIG. 1 is an illustrative partial side view of an endoscope formed in accordance with the present invention and including a plurality of image capturing means, a plurality of illumination means, and a plurality of non-visual sensor means, wherein each image capturing means is grouped with one illumination means and one non-visual sensor means, with each respective grouping being arranged in circumferentially and axially spaced relation to one another in the side wall of the endoscope at the distal end thereof.
Figures 2, 3A, 3B, 3C:
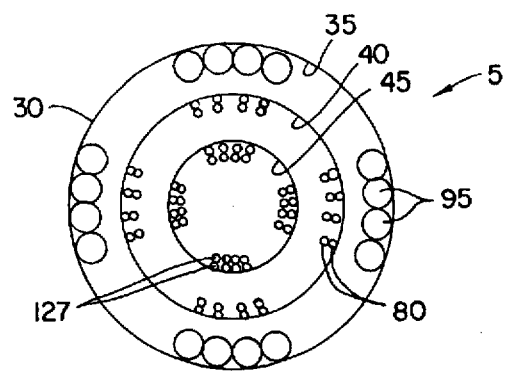
FIG. 2 is an illustrative cross-sectional view taken along line 2—2 of FIG. 1, showing the various connecting means which connect the various image capturing means, illumination means and non-visual sensor means to the proximal end of the endoscope.
FIGS. 3A, 3B and 3C are illustrative views showing various images which may be generated by the endoscope of FIG. 1.

Referring now to FIGS. 1 and 2, an endoscope 5 is shown which comprises one preferred embodiment of the present invention. Endoscope 5 generally comprises an elongated shaft 10 having a longitudinal axis 12, a distal end 15 terminating in a distal end surface 20, a proximal end 25, and an outer side wall 30 extending between distal end 15 and proximal end 25. Shaft 10 may or may not be flexible, depending on the particular application involved. A plurality of interior passageways (representatively shown as concentric passageways 35, 40 and 45 in FIG. 2) extend longitudinally through shaft 10.

Endoscope 5 also comprises a plurality of image capturing means 55 which are disposed about the shaft's distal end 15. Each of the image capturing means 55 faces substantially radially outwardly from the distal end of the shaft, through an opening 60 formed in the shaft's outer side wall 30. Each of the image capturing means 55 is adapted to capture an image of any objects and/or structures located within a predetermined field of view 65 associated with that image capturing means. Preferably a sufficient number of image capturing means 55 are provided on the distal end of the endoscope so that their individual fields of view 65 will collectively provide substantially complete coverage of the entire region surrounding the distal end of the endoscope.

Each of the image capturing means 55 comprises a charge coupled device ("CCD") element 70 and an associated lens means 75. Each CCD element 70 is arranged so that its light-receiving surface faces substantially radially outwardly through one of the shaft's openings 60. The associated lens means 75 for that CCD element is located in, or in association with, the same opening 60 so as to establish the effective field of view for that CCD element. In this way, each CCD element 70 will receive a visual image of any objects and/or structures located within the field of view 65 established for that CCD element by its associated lens means 75.

Each image capturing means 55 is adapted to convert the image information received by its CCD element 70 into corresponding electrical signals. These electrical signals are transmitted by connecting means 80 through the interior of shaft 10 to image processing means 85 which are located adjacent to the proximal end of the shaft. Preferably connecting means 80 comprise wires which extend between each CCD element 70 and image processing means 85, with the wires extending through the shaft's interior passageway 40 (see FIG. 2).

Endoscope 5 also comprises a plurality of illumination means 90 for providing illumination for the image capturing means 55. In the embodiment shown in FIGS. 1 and 2, one illumination means 90 is provided for each image capturing means 55, with that illumination means 90 being grouped with its associated image capturing means 55 so as to illuminate the field of view for that particular image capturing means. Each illumination means 90 preferably comprises a bundle 95 of elongated fiber optic filaments. Each bundle 95 of fiber optic filaments extends from the proximal end of the endoscope to an opening 100 located in the distal end of the endoscope. The opening 100 provided for each illuminating means 90 is located adjacent to the opening 60 which is provided for its associated image capturing means 55. In the embodiment shown in FIGS. 1 and 2, each bundle 95 of fiber optic filaments extends through interior passageway 35 (see FIG. 2).

A light source 105 is located adjacent to the proximal ends of fiber optic bundles 95. Light from light source 105 enters the proximal ends of fiber optic bundles 95 and is transmitted along the length of the bundles to the distal ends thereof, where it exits from the endoscope through the various openings 100. Preferably diffusing lens means 110 are provided at each opening 100 so as to properly diffuse the light passing out of the distal ends of fiber optic bundles 95. In this way the light provided by each of the illumination means 90 will illuminate the field of view for the image capturing means 55 which is associated with that particular illumination means.

Endoscope 5 also comprises a plurality of non-visual sensor means 115. These non-visual sensor means 115 are adapted to provide additional non-visual information about any objects and/or structures located close to the endoscope's visual sensors. In the embodiment shown in FIGS. 1 and 2, one non-visual sensor means 115 is provided for each image capturing means 55, with that non-visual sensor means 115 being grouped with its associated image capturing means 55 so as to provide additional non-visual information about any objects and/or structures which may be located in the field of view for that image capturing means 55. Each non-visual sensor means 115 comprises a sensor element 120 which faces outboard of shaft 10 through an opening 125 formed in the shaft's side wall 30. Each sensor element 120 is connected by connecting means 127 to signal processing means 130 which are located at the proximal end of the shaft. Preferably each non-visual sensor element 126 is connected to signal processing means 130 by a plurality of wires 127, with the wires 127 extending through the shaft's interior passageway 45 (see FIG. 2).

The specific type of non-visual sensor element 120 incorporated in endoscope 5 will depend upon the particular application involved. For example, in some situations it may be desirable to obtain ultrasound information about any objects and/or structures being viewed by the endoscope through its image capturing means 55. In this case non-visual sensor elements 120 would comprise ultrasound transducers, and signal processing means 130 would comprise apparatus of the sort well known in the art adapted to process the output signals obtained from the ultrasound transducers so as to derive meaningful information from the same. Alternatively, non-visual sensor elements 120 might comprise temperature sensors, pressure sensors, chemical sensors, radiation sensors and/or any other type or types of sensors appropriate for a particular application, and signal processing means 130 would then comprise corresponding apparatus of the sort well known in the art adapted to process the output signals obtained from such other sensors and derive meaningful information from the same. The output from signal processing means 130 is fed into image processing means 85 by connecting means 140.

Image processing means 85 are adapted to receive the various images generated by image capturing means 55 and to visually display the same, one or more at a time, on a display 145. Alternatively, or concurrently, image processing means 85 may also convey those images to a recording device such as a VCR or computer memory. To this end, image processing means 85 generally comprise a preprogrammed digital computer and appropriate user interface controls through which the operator may direct the image processing means. Image processing means 85 are connected to each of the image capturing means 55 by connecting means 80, and image processing means 85 are connected to display 145 by connecting means 150.

As illustratively shown in FIGS. 3A–3C, the image provided on display 145 may comprise a single image generated by a selected one of the image capturing means 55, e.g. the image generated by image capturing means 55A as shown in FIG. 3A, or the image generated by image capturing means 55B as shown in FIG. 3B. Alternatively, the image provided on display 145 may comprise a plurality of images generated by selected ones of the image capturing means 55, all displayed simultaneously in a tiled or seamlessly integrated fashion, e.g. the image provided on display 145 may comprise a composite of the images generated by image capturing means 55B, 55A, 55F and 55E, as shown in FIG. 3C. It will be appreciated that such a composite image may take any one of many different formats, as preferred by the user.

More particularly, as noted above and as illustrated in FIG. 2, connecting means 80 connect image processing means 85 to the output signals from each one of the image capturing means 55. Thus, image processing means 85 is able to access any one or ones of the various images generated by the numerous image capturing means, as required to generate the desired display image. Accordingly, it is a relatively simple matter, and well within the ability of a person skilled in the art, to construct appropriate image processing means which will select, process and display images obtained from a selected one or ones of the image capturing means 55, as directed by the operator using appropriate user interface controls. Furthermore, the selected image or images can be changed at will by the operator using those same user interface controls, thereby allowing the operator to select whatever field or fields of view as may be desired at any given time. In addition, it will be appreciated that in the situation where composite images are involved, the format of the display can be changed at will by the operator using those same user interface controls. Thus it will be seen that, by initially positioning endoscope 5 at a surgical site at the outset of a procedure, the operator can thereafter electronically select the specific field or fields of view which are to be viewed through the endoscope. As a result, the operator can observe all aspects of the surgical site without any repositioning of the endoscope.

It is to be appreciated that the non-visual information derived by signal processing means 130 from non-visual sensor means 115 is also fed to image processing means 85. Using conventional techniques well known in the art, the image processing means 85 can combine this additional non-visual information with the visual images obtained by image capturing means 55 so as to supplement or enhance those visual images. By way of example, suppose endoscope 5 is being used inside a knee joint to view meniscal cartilage, and suppose further that non-visual sensor means 115 comprise ultrasound sensors of the type adapted to determine tissue thickness. In such a case, the visual images obtained by image capturing means 55 might be enhanced in image processing means 85 using the ultrasound information derived by signal processing means 130. Thus, the visual images obtained by image capturing means 55 might be color-coded (using the data derived by signal processing means 130) so as to indicate the thickness of the cartilage at different locations.

It will, of course, be appreciated that the endoscope 5 shown in FIGS. 1 and 2 can be modified somewhat without departing from the scope of the present invention. Thus, for example, in the endoscope 5 shown in FIGS. 1 and 2, each of the image capturing means 55 has one illumination means 90 and one non-visual sensor means 115 associated with it. However, it will be appreciated that the various image capturing means 55, illumination means 90 and non-visual sensor means 115 need not necessarily be grouped together in this way. Thus, for example, the number of illumination means 90 and/or the number of non-visual sensor means 115 can be more or less than the number of image capturing means 55, and their placement need not necessarily be grouped with specific image capturing means. Indeed, to the extent that satisfactory illumination is already provided at the surgical site, either by a separate illumination device or by the ambient light at the site, illumination means 90 may even be omitted entirely. Furthermore, to the extent that non-visual information is not desired, non-visual sensor means 115 can also be omitted entirely.

Furthermore, in the endoscope 5 shown in FIGS. 1 and 2, each of the image capturing means 55 comprises a CCD element 70 and a lens means 75, where the lens means 75 is placed in an opening 60 formed in the shaft's side wall 30, and the CCD element 70 is placed immediately adjacent to lens means 75. Connecting means 80 then connect the outputs of CCD elements 70 to image processing means 85. Thus, with this design, the CCD elements 70 are disposed along shaft 10, adjacent to each side wall opening 60. However, if desired, the CCD elements 70 can be moved to the proximal end of shaft 10, and a plurality of fiber optic bundles can be used to carry an image from a particular lens means 75 to its corresponding CCD element 70. In such a case these image-carrying bundles could extend through the shaft's interior passageway 40 in much the same way that connecting means 80 pass through interior passageway 40 in FIG. 2.

Furthermore, with the endoscope 5 shown in FIGS. 1 and 2, a plurality of image capturing means 55 are shown. Of course, the precise number and spacing of these image capturing means may be varied in accordance with the application at hand, without departing from the scope of the present invention. In general, and as noted above, it is preferred that the image capturing means 55 be sufficient in number and spacing so that their respective fields of view 65 will collectively provide substantially complete coverage of the region surrounding the distal end of the endoscope.

In the embodiment shown in FIG. 1, the fields of view 65 for the various image capturing means 55 are shown as not overlapping one another. Of course, it will be appreciated that the fields of view 65 may be made to overlap one another if desired, merely by adjusting the spacing between adjacent image capturing means 55 and/or by adjusting the construction of the lens means 75 placed in front of each CCD element 70.

Figure 4:
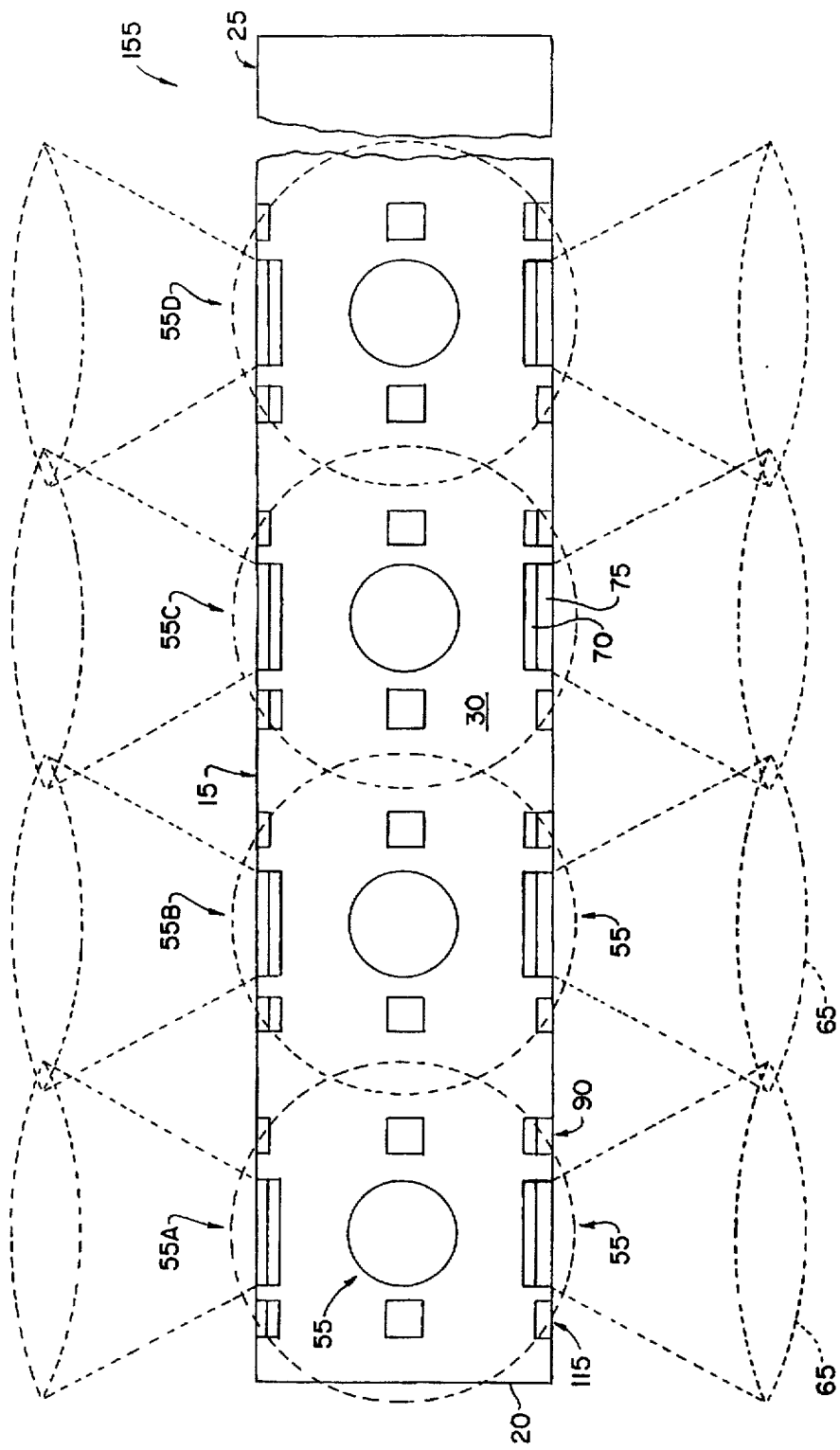
FIG. 4 is an illustrative partial side view showing another embodiment of the present invention, wherein the embodiment is generally similar to the embodiment shown in FIG. 1, except that the fields of view of adjacent image capturing means slightly overlap one another.

Thus, for example, FIG. 4 shows another endoscope 155 also formed in accordance with the present invention. Endoscope 155 is substantially identical to the endoscope 5 previously discussed, except that endoscope 155 has its image capturing means 55 positioned, and its lens means 75 formed, so that the field of view 65 for each image capturing means 55 slightly overlaps the fields of view 65 for its adjacent image capturing means 55. As a result of this construction, when the operator moves from the field of view for one image capturing means 55A (see FIG. 5A) to the field of view for an adjacent image capturing means 55B (see FIG. 5B), some image redundancy will be seen by the operator. This can help the operator establish the proper frame of reference for a given display, if the displays are being sequenced from one field of view to a neighboring field of view. Similarly, when the operator selects a display format combining the images from two or more adjacent image capturing means, e.g. the images associated with the image capturing means 55A and 55B as seen in FIG. 5C, the relatively small amount of overlap between the two or more images can be used by image processing means 85 to properly register the several images relative to one another. Furthermore, by virtue of the fact that adjacent image capturing means 55 have overlapping fields of view, image processing means 85 can also be constructed so as to generate a moving image which can be panned across the surgical site in response to operator commands for the same. Thus, the operator can essentially pan the endoscope about the surgical site at will so as to examine any areas of interest, without ever moving the endoscope from an initially established position.

Figure 6:
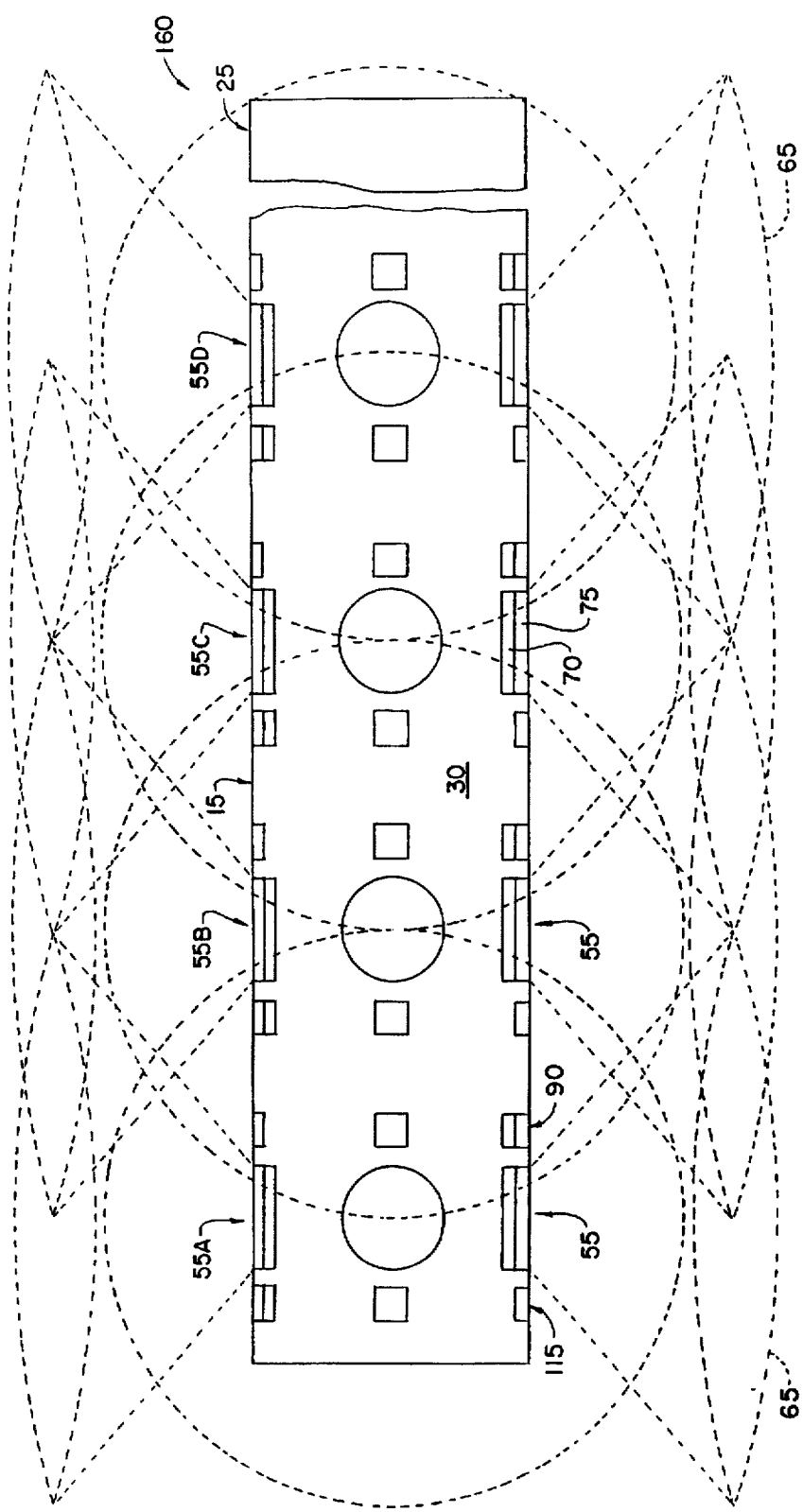
FIG. 6 is an illustrative partial side view showing another embodiment of the present invention, wherein the embodiment is generally similar to the embodiments shown in FIGS. 1 and 4, except that the fields of view of adjacent image capturing means significantly overlap one another.

FIG. 6 shows another endoscope 160. Endoscope 160 is substantially identical to endoscope 5 shown in FIG. 1 and to endoscope 155 shown in FIG. 4, except that endoscope 160 has its image capturing means 55 positioned, and its lens means 75 formed, so that the field of view for each image capturing means 55 significantly overlaps the fields of view for its neighboring image capturing means 55. As a result of this construction, when the operator moves from the field of view for one image capturing means 55A (see FIG. 7A) to the field of view for an adjacent image capturing means 55B (see FIG. 7B), significant image redundancy will be seen by the operator. Similarly, when the operator selects a display combining the images from two or more adjacent image capturing means, e.g. the images associated with the image capturing means 55A and 55B as seen in FIG. 7C, there will be a very substantial amount of overlap between the simultaneously-displayed images. By taking advantage of this feature, image processing means 85 can generate stereoscopic views (see FIG. 7D) on display 145 by using the overlapping fields of view of two adjacent image capturing means 55 in ways well known in the art. Display means 145 may be adapted to provide distinct views to the left and right eyes using one of a variety of stereoscopic display means well known in the art.

With the endoscopes 5, 155 and 160 shown in FIGS. 1, 4 and 6, respectively, the fields of view 65 for each of the image capturing means 55 are shown to be substantially the same as one another. However, it should be appreciated that this does not necessarily need to be the case. More particularly, inasmuch as each of the image capturing means 55 has its own lens means 75 associated therewith, these lens means 75 can be varied from one another as desired so as to give each of the image capturing means 55 the desired field of view. Thus, for example, the image capturing means 55 disposed closer to distal end surface 20 might be given a narrower field of view coupled with a higher optical magnification, whereas the image capturing means 55 disposed further from distal end surface 20 might be given a wider field of view coupled with a lesser optical magnification. Other arrangements of this type will be obvious to those skilled in the art.

Similarly, to the extent that they are provided, the non-visual sensor means 115 need not all be the same as one another. For example, some of the non-visual sensor means 115 provided on an endoscope might be ultrasound sensors, while others of the non-visual sensor means 115 on the same endoscope might be temperature sensors.

Furthermore, with endoscopes 5, 155 and 160 shown in FIGS. 1, 4 and 6, respectively, all of the image capturing means 55 are shown as being directed substantially radially outboard of the endoscope's side wall 30. It is to be understood, however, that the present invention is not limited to such devices. Thus, for example, the image capturing means 55 could be directed obliquely outboard from the side wall of the endoscope. Similarly, to the extent that they are provided, illumination means 90 and non-visual sensor means 115 could be likewise directed.

In addition to the foregoing, the image capturing means 55 (and/or illumination means 90 and/or non-visual sensor means 115) can also be mounted in the distal end surface of the endoscope so as to be directed at the area located distally of the endoscope. Thus, for example, additional image capturing means 55 (and/or illumination means 90 and/or non-visual sensor means 115) can be mounted in the substantially planar distal end wall 20 of endoscopes 5, 155 and 160 shown in FIGS. 1, 4 and 6, respectively. In such an arrangement, these additional image capturing means 55 (and/or illumination means 90 and/or non-visual sensor means 115) could be oriented so that they are aligned with the endoscope's longitudinal axis 12, or they could be oriented so that they face at an oblique angle to the endoscope's longitudinal axis 12. Alternatively, the image capturing means 55 (and/or illumination means 90 and/or non-visual sensor means 115) can be disposed in a distal end wall having a configuration other than the substantially planar one shown in the endoscopes 5, 155 and 160 of FIGS. 1, 4 and 6, respectively.

More particularly, and looking now at FIGS. 8 and 9, the distal end wall 165 of an endoscope 170 is shown. Endoscope 170 may be any one of the endoscopes 5, 155 and 160 shown in FIGS. 1, 4 and 6, respectively, modified as hereinafter described, or it may be some other endoscope having an elongated shaft. In any case, a semispherical end wall 165 closes off the distal end of the endoscope. A plurality of image capturing means 55 (preferably each with an associated illumination means 90 and a non-visual sensor means 115) are also provided. Preferably the image capturing means 55 are disposed in semispherical end wall 165 so that their fields of view overlap one another slightly. In this way the plurality of image capturing means 55 disposed in semispherical end wall 165 will collectively form a sort of fisheye arrangement. As a result of this construction, when the operator moves from the field of view for one image capturing means 55Q (see FIG. 10A) to the field of view for an adjacent image capturing means 55R (see FIG. 10B), some image redundancy will be seen. Similarly, when the operator selects a display combining the images from two or more adjacent image capturing means, e.g. the images associated with image capturing means 55Q and 55R as seen in FIG. 10C, there will be some overlap between the simultaneously displayed images. By combining the images associated with image capturing means 55Q, 55R, 55S, 55T and 55U, a fisheye type of image may be generated (see FIG. 10D). Of course, it should also be appreciated that image capturing means 55 can be arranged in semispherical end wall 165 so as to have substantially no image overlap, or the image capturing means 55 can be arranged so as to have significant image overlap, whereby stereoscopic views can be generated.

Looking next at FIGS. 11 and 12, another endoscope 175 is shown which is also formed in accordance with the present invention. Endoscope 175 comprises an elongated shaft 180 having a longitudinal axis 185, a distal end 190 terminating in an annular end surface 195, a proximal end 197, and a passageway 200 extending between distal end 190 and proximal end 197. An image capturing means 202 is disposed at the distal end of the endoscope. More particularly, image capturing means 202 comprises a semispherical lens means 205 located adjacent to the shaft's annular distal end surface 195, and a substantially planar CCD element 210 disposed within interior passageway 200 so as to be adjacent to and substantially coplanar with annular distal end surface 195. CCD element 210 is arranged so that its light-receiving cells 215 (FIG. 12) face distally towards semispherical lens 205. Connecting means 220 connect the output of CCD element 210 to image processing means 225, which are in turn connected to a display 230 by connecting means 235. Image processing means 225 generally comprise a preprogrammed digital computer and appropriate user controls through which the operator may direct the image processing means. As a result of this construction, semispherical lens means 205 will focus an image of a broad field of view 240 onto the planar CCD element 210. Accordingly, the image of any objects and/or structures located within field of view 240 will be received by the CCD element's light-receiving cells 215 and converted into corresponding electrical signals. These signals are then fed into image processing means 225 for selection, processing and display on display 230.

More particularly, by appropriately programming image processing means 225, the operator will be able to view on display 230 either the complete fisheye image captured by lens means 205 or some limited portion thereof. In this respect it is to be appreciated that in some circumstances the full image captured by lens means 205 may be too large or too complex to be viewed all at once on display 230. In this case, the operator may command image processing means 225 (using appropriate user interface controls) to display the output from only some of the CCD element's cells 215 on display 230. For example, the operator may instruct image processing means 225 to display the output from the cell matrix 240 shown in FIG. 12, where cell matrix 240 comprises a subset of the full set of cells making up CCD element 210. This will in turn cause only a portion of the full image captured by lens means 205 to be displayed on display 230. Furthermore, by providing appropriate user interface controls, the operator can also instruct image processing means 225 to alter the subset of CCD cells 215 being monitored, so as to change the image being displayed on display 230. Thus it will be seen that by providing the operator with appropriate user interface controls, the operator can instruct image processing means 225 to dynamically "move" its active cell matrix 240 about the surface of CCD element 210 so as to effectively change the image being displayed on display 230. In this way the image being presented on display 230 can be electronically steered by the operator using appropriate user interface controls, all without the endoscope ever being moved from an initially established position at a surgical site.

With the design of FIGS. 11 and 12, CCD element 210 is located at the distal end of shaft 180, adjacent to semispherical lens 205. However, if desired, CCD element 210 can be moved to the proximal end of shaft 180, and a plurality of fiber optic filaments or a rod-lens system of the sort well known in the art can be used to carry the image from semispherical lens 205 to CCD element 210. Illumination means may also be provided on endoscope 175 if desired.

Figure 14:
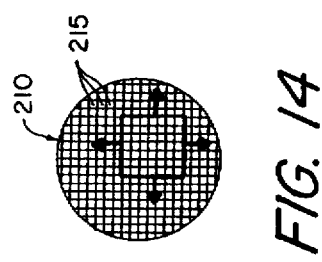
FIG. 14 is an illustrative cross-sectional view taken along line 14—14 of FIG. 13.
Figure 13:
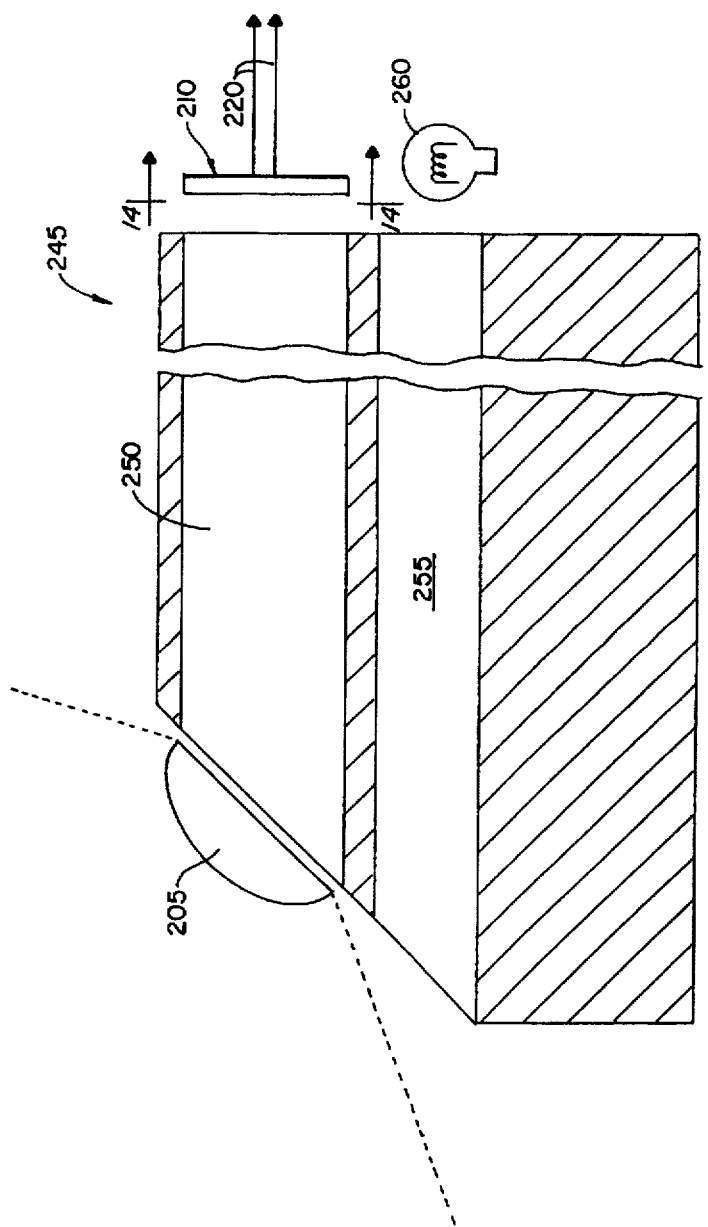
FIG. 13 is an illustrative side view showing the distal end of yet another endoscope formed in accordance with the present invention, wherein a fisheye lens is disposed at the distal end of the endoscope so as to be slanted at an oblique angle relative to the longitudinal axis of the endoscope, and a bundle of fiber optic filaments conveys the image captured by the fisheye lens to a CCD element disposed at the proximal end of the endoscope.

A variation of the concept shown in FIGS. 11 and 12 is shown in FIGS. 13 and 14. More specifically, an endoscope 245 is shown which has its semispherical lens means 205 disposed at an oblique angle relative to the longitudinal axis of the endoscope. A bundle 250 of fiber optic filaments conveys the image captured by lens means 205 through the endoscope's shaft to the CCD element 210, which is disposed at the proximal end of the endoscope. Connecting means 220 feed the output of the CCD element's individual cells 215 to image processing means 225. Another bundle 255 of fiber optic filaments may be used to deliver light from light source 260 to the region being viewed. As with the endoscope 180 shown in FIGS. 11 and 12, an operator using the endoscope 245 shown in FIGS. 13 and 14 can view the entire image captured by lens means 205 or some reduced portion thereof. Furthermore, in this latter case, by properly instructing image processing means 225 using appropriate user interface controls, the operator can electronically alter the portion of the image being displayed through display 230, so as to electronically "steer" the endoscope to the region of interest. In addition to the foregoing, it will also be appreciated that with the endoscope 245 shown in FIGS. 13 and 14, the operator will also be able to manually adjust the image being observed by the endoscope by rotating the endoscope about its longitudinal axis, since this will cause the endoscope's obliquely oriented lens to change its direction of view.

If desired, the bundle 250 of fiber optic filaments shown in FIG. 13 can be replaced with an equivalent rod-lens arrangement, where a plurality of rod-lens elements convey the image captured by lens means 205 through the endoscop's shaft to the CCD element 210. Alternatively, the CCD element 210 can be moved down to the distal end of the endoscope adjacent to lens means 205, and the bundle 250 of fiber optic filaments omitted entirely. In this arrangement connecting means 220 would extend through the body of the endoscope so as to connect CCD element 210 to image processing means 225.

It is also anticipated that one might place a fly's eye lens in front of the endoscope's CCD element. More particularly, and looking next at FIG. 15, an endoscope 260 is shown. Endoscope 260 comprises a plurality of image capturing means 265 and a plurality of illumination means 270. Each of the image capturing means 265 comprises a CCD element 275 having a substantially planar array of light-receiving CCD cells, and a fly's eye lens 280 having a plurality of separate focusing elements 283. Preferably CCD element 275 is disposed adjacent to fly's eye lens 280 so that one or more of the CCD element's light-receiving cells is aligned with one of the fly's eye lens' focusing elements 283. In one preferred embodiment, a plurality of CCD cells are aligned with each of the focusing elements 283.

Figure 15:
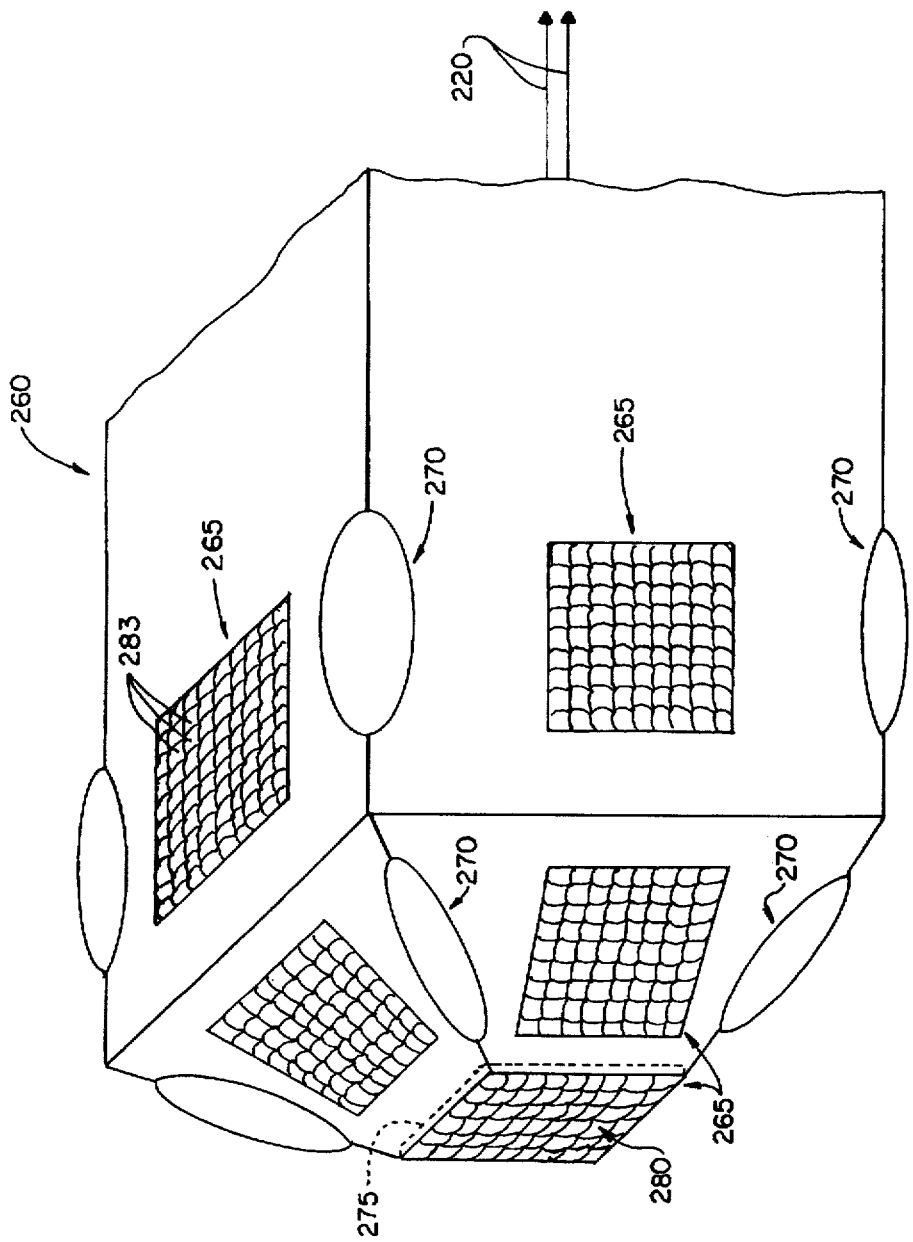
FIG. 15 is an illustrative side view showing the distal end of yet another endoscope formed in accordance with the present invention, wherein the endoscope comprises a plurality of image capturing means, each of which includes a fly's eye lens having a plurality of separate focusing elements.

With the endoscope 260 shown in FIG. 15, each of the image capturing means 265 is connected to appropriate image processing means by connecting means 220. These image processing means are adapted so that the operator can select which one or ones of the images from one or more of the image capturing means 265 are to be displayed on a screen, wherein the image from a particular image capturing means can comprise the signals from some or all of its CCD cells.

A variation of this concept is shown in FIG. 16. More particularly, an endoscope 285 is shown which comprises a single image capturing means 265 and a plurality of illumination means 270. The image capturing means 265 comprises a CCD element 275 having a substantially planar array of light-receiving CCD cells, and a fly's eye lens 280 having a plurality of separate focusing elements 283. Again, CCD element 275 is preferably disposed adjacent to the fly's eye lens 280 so that one or more of the CCD element's light-receiving cells is aligned with one of the fly's eye lens' focusing elements 283.

Still another variation of this concept is shown in FIG. 17. More particularly, an endoscope 290 is shown which comprises a single image capturing means 295. Image capturing means 295 comprises a CCD element 300 having a substantially semispherical array of light-receiving CCD cells, and a semispherical fly's eye lens 305 having a plurality of separate focusing elements 310. CCD element 300 is preferably disposed adjacent to fly's eye lens 305 so that one or more of the CCD element's light-receiving cells is aligned with one of the fly's eye lens' focusing elements 310.

With the endoscopes 285 and 290 of FIGS. 16 and 17, respectively, image capturing means 265 and 295 are connected to appropriate image processing means by connecting means 220. These image processing means are adapted so that the operator can select the image to be viewed from the set of some or all of the CCD element's light receiving cells.

Figure 18:
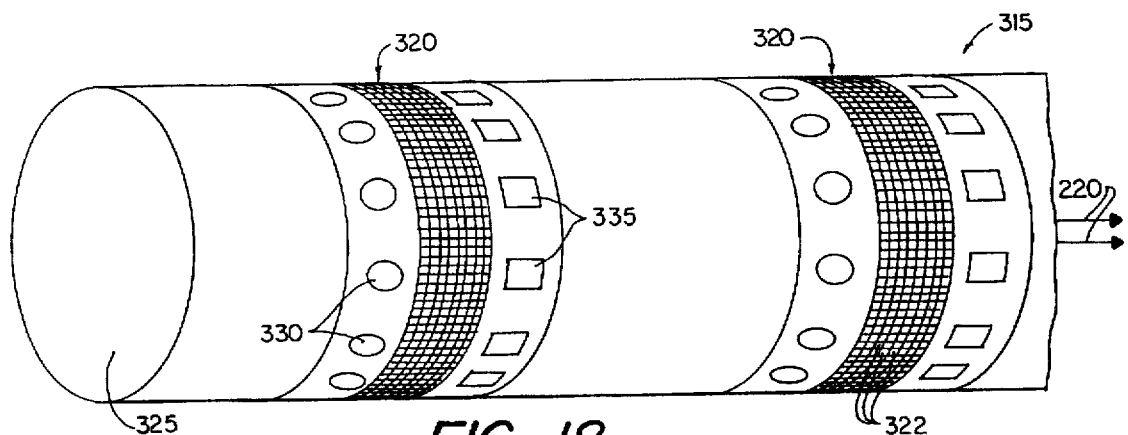
FIG. 18 is an illustrative side view showing the distal end of yet another endoscope formed in accordance with the present invention, wherein axially spaced bands of CCD cells circumferentially surround the distal portion of the endoscope, each band of CCD cells being flanked by a band of circumferentially spaced illumination means on one side thereof, and a band of circumferentially spaced non-visual sensor means on the other side thereof.

An endoscope can also be formed in which the image capturing means comprise continuous arrays of CCD cells positioned on the side wall of the endoscope. More particularly, and looking next at FIG. 18, an endoscope 315 is shown in which continuous bands 320 of CCD cells 322 extend circumferentially around the distal end of the endoscope's shaft. Appropriate lens elements (not shown) are preferably positioned over CCD cells 322. In the embodiment shown in FIG. 18, CCD bands 320 are longitudinally spaced from each other and from the distal end surface 325 of endoscope 315. These bands 320 may be flanked at their distal and proximal edges by radially aligned and circumferentially spaced pluralities of illuminating means 330 and non-visual sensor means 335, respectively. CCD cells 322 are connected to appropriate image processing means by connection means 220. The foregoing configuration permits the operator to access images of substantially all locations disposed radially of CCD bands 320, by selectively reading the output of the appropriate CCD cells 322.

Figure 19:
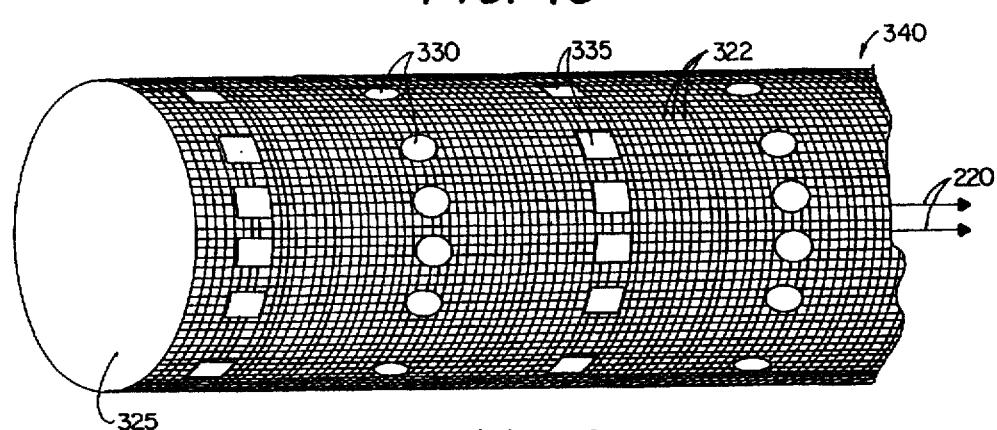
FIG. 19 is an illustrative side view showing the distal end of still another endoscope formed in accordance with the present invention, wherein the endoscope is generally similar to that shown in FIG. 18, except that the CCD cells cover substantially the entire outer side wall of the distal end of the shaft, and wherein illumination means and non-visual sensor means extend through the CCD array at spaced locations.
Figure 20:
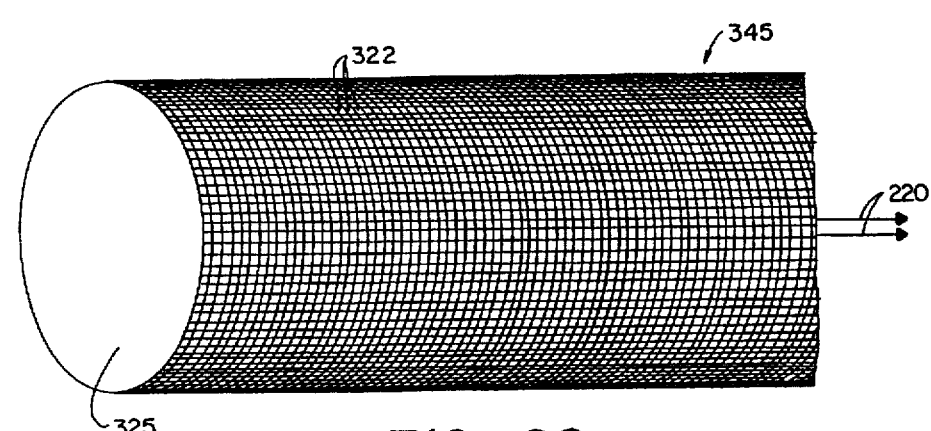
FIG. 20 is an illustrative side view showing the distal end of yet another endoscope formed in accordance with the present invention, wherein the endoscope is generally similar to that shown in FIG. 19, except that the illumination means and the non-visual sensor means have been omitted.

Of course, the spacing of bands 320 may be as close together, or as far apart, as desired. Therefore, in the case shown in FIG. 19, the entire distal end of the endoscope 340 may be covered by an array of CCD cells 322, except for where illumination means 330 and/or non-visual sensor means 335 project through the array. Alternatively, illumination means 330 and non-visual sensor means 335 may be omitted entirely from the endoscope, as in the case of endoscope 345 shown in FIG. 20. In the latter case, illumination of the volume surrounding endoscope 345 (which would constitute the total possible viewing field of the device) would be provided either by separate illumination means or by the ambient conditions of the environment in which the endoscope is being used. Again, with the endoscopes 315, 340 and 345 of FIGS. 18–20, CCD cells 322 are connected to appropriate image processing means by connection means 220, where the image processing means are adapted to access the output signals from any subset of the cells 322. Furthermore, it is to be appreciated that with the endoscopes 315, 340 and 345 of FIGS. 18–20, appropriate lens elements (not shown) are preferably positioned over CCD cells 322. Also, it should be appreciated that the endoscopes 315, 340 and 345 could have their distal end surfaces 325 covered with CCD cells 322 as well.

It will be appreciated that the internal diameter of a standard endoscope is limited. Accordingly, in those situations where it is desired to utilize a large number of CCD elements and/or non-visual sensor means on the endoscope, the number of separate connecting means extending between these elements and their associated processing means may become too large to fit conveniently through the shaft of the endoscope. In this case, the various outputs from the image capturing means and/or the non-visual sensor means may be multiplexed, as representatively shown in FIG. 21. More particularly, a plurality of representative CCD elements 70 are shown in FIG. 21. The outputs from these CCD elements 70 are multiplexed through a multiplexor 350 so that their output signals can be transmitted through the endoscope's shaft by a reduced number of wires 352. A control line 354 connected to image processing means 85 controls the operation of multiplexor 350. Of course, other means will also be apparent to those skilled in the art for reducing the number of wires extending through the endoscope's shaft.

It is also to be understood that the image capturing means 55 may be disposed in the openings 60 in a variety of different ways. For example, the lens means 75 and CCD element 70 may be disposed in the side wall 30 of the endoscope such that the outer surface of the lens means is recessed slightly relative to side wall 30, as shown in FIG. 22. Alternatively, the lens means 75 and CCD element 70 might be located in side wall 30 such that the outer surfaces of the lens means are disposed substantially flush with side wall 30, as shown in FIG. 23. Finally, the lens means 75 and CCD element 70 might be located in side wall 30 such that the outer surfaces of the lens means are disposed outboard of side wall 30, as shown in FIG. 24.

Furthermore, while in the foregoing description the invention has been described principally in the context of comprising an improved endoscope for use in a remote surgical site, it will also be appreciated that the present invention is equally applicable to viewing devices used in a wide variety of other applications. Thus, for example, the present invention might be incorporated in a viewing system used to examine the interiors of pipelines or nuclear reactors or large complex machines such as jet engines. Furthermore, the present invention might be incorporated in portable video cameras or video security systems so as to provide electronically steerable lens systems for the same. These and other applications of this type will be obvious to persons skilled in the art.

Numerous other alterations, modifications, variations, changes and the like will also be apparent to those skilled in the art, in view of the foregoing description of the invention. Accordingly, it should be understood that the foregoing description has been presented by way of illustration and not by way of limitation. The scope of the present invention is intended to be limited only by the terms of the appended claims.

What is claimed is:

1. An endoscope comprising:

an elongated shaft, said elongated shaft having a distal end terminating in a distal end surface, a proximal end, an outer side wall extending from said distal end to said proximal end, and at least one internal passageway extending from said distal end to said proximal end;

image capturing means associated with said distal end of said shaft so as to face outwardly therefrom, said image capturing means defining a field of view associated therewith, and said image capturing means being adapted to capture an image of any objects located within its said field of view and to convert that image into corresponding signals, wherein said image capturing means comprises a CCD element forming a circumferential band about said distal portion of said shaft, said CCD element comprising a plurality of CCD cells, and further wherein said corresponding signals are made up of the output from each one of said CCD cells; and processing means associated with said proximal end of said shaft and connected to said CCD cells, said processing means being adapted to (i) use the outputs from all of said CCD cells so as to generate a display of the image captured by said image capturing means, and (ii) use the outputs from only selected ones of said CCD cells so as to generate a display of a selected portion of the image captured by said image capturing means.

2. An endoscope according to claim 1 wherein a plurality of illumination means are disposed in a circumferentially spaced array adjacent to said CCD element on at least one side thereof.

3. An endoscope according to claim 1 wherein a plurality of non-visual sensing means are disposed in a circumferentially spaced array adjacent to said CCD element on at least one side thereof.

4. An endoscope comprising:

an elongated shaft, said elongated shaft having a distal end terminating in a distal end surface, a proximal end, an outer side wall extending from said distal end to said proximal end, and at least one internal passageway extending from said distal end to said proximal end;

image capturing means associated with said distal end of said shaft so as to face outwardly therefrom, said image capturing means defining a field of view associated therewith, and said image capturing means being adapted to capture an image of any objects located within its said field of view and to convert that image into corresponding signals, wherein said image capturing means comprises a CCD element covering substantially all of said outer side wall of said shaft adjacent to said distal end, said CCD element comprising a plurality of CCD cells, and further wherein said corresponding signals are made up of the output from each one of said CCD cells; and processing means associated with said proximal end of said shaft and connected to said CCD cells, said processing means being adapted to (i) use the outputs from all of said CCD cells so as to generate a display of the image captured by said image capturing means, and (ii) use the outputs from only selected ones of said CCD cells so as to generate a display of a selected portion of the image captured by said image capturing means.

5. An endoscope according to claim 4 wherein said CCD element also covers said distal end surface of said shaft.

* * * * *